US012606835B2

(12) United States Patent (10) Patent No.: US 12,606,835 B2
Mao et al. (45) Date of Patent: Apr. 21, 2026

(54) AUTO-INDUCTION REGULATORY SYSTEM BASED ON QUORUM SENSING AND APPLICATION THEREOF

(71) Applicant: OCEAN UNIVERSRRY OF CHINA, Qingdao (CN)

(72) Inventors: Xiangzhao Mao, Qingdao (CN); Zhen Liu, Qingdao (CN); Zhuoning Cao, Qingdao (CN)

(73) Assignee: OCEAN UNIVERSRRY OF CHINA, Qingdao (CN)

( * ) Notice: Subject to any disclaimer, the term of this patent is extended or adjusted under 35 U.S.C. 154(b) by 943 days.

(21) Appl. No.: 17/855,849

(22) Filed: Jul. 1, 2022

(65) Prior Publication Data

US 2022/0411807 A1     Dec. 29, 2022

(30) Foreign Application Priority Data

Sep. 29, 2021    (CN) .......................... 202111147902.4

(51) Int. Cl.
| | |
|---|---|
| *C12N 15/70* | (2006.01) |
| *C07K 14/435* | (2006.01) |
| *C12N 9/02* | (2006.01) |
| *C12N 9/16* | (2006.01) |
| *C12N 9/88* | (2006.01) |

(52) U.S. Cl.
CPC ........ *C12N 15/70* (2013.01); *C07K 14/43595* (2013.01); *C12N 9/0069* (2013.01); *C12N 9/16* (2013.01); *C12N 9/88* (2013.01); *C12Y 113/12007* (2013.01); *C12Y 402/02003* (2013.01); *C12N 2830/002* (2013.01)

(58) Field of Classification Search
CPC .................................................... C12N 15/70
See application file for complete search history.

(56) References Cited

U.S. PATENT DOCUMENTS

| | | | |
|---|---|---|---|
| 10,590,426 B2 * | 3/2020 | Ducat | .................... C12N 15/74 |
| 2018/0110266 A1 | 4/2018 | Lee et al. | |
| 2019/0079913 A1 | 3/2019 | Levine et al. | |
| 2020/0138123 A1 | 5/2020 | Nordstrom et al. | |

FOREIGN PATENT DOCUMENTS

| | | | | |
|---|---|---|---|---|
| WO | WO-2006116400 A2 * | 11/2006 | ......... | C12N 15/1086 |
| WO | WO-2011055987 A2 * | 5/2011 | ............. | C12N 15/63 |

OTHER PUBLICATIONS

Kylilis et al., Jul. 11, 2018, Nature Communications, (2018)9:2677, p. 1-9 and Supplementary Information (Year: 2018).*
"Part: BBa_J23100," Registry of Standard Biological Parts, available "Aug. 4, 2006," accessed May 6, 2025 (Year: 2006).*
Prindle et al., Dec. 18, 2011, Nature, 481, 39-44 (2012), p. 39-44 and Supplementary Information) (Year: 2011).*

* cited by examiner

*Primary Examiner* — Soren Harward
*Assistant Examiner* — Jenna L Persons
(74) *Attorney, Agent, or Firm* — Hemisphere Law, PLLC

(57) ABSTRACT

Disclosed is an auto-induction regulatory system based on quorum sensing, comprising luxI, luxR and egfp, wherein, the promoter for controlling the expression of luxI and luxR is selected from $P_{luxI}$, $P_{BB}$ or $P_{J23100}$; the promoter for controlling the expression of egfp is selected from $P_{luxI}$, $P_{luxI}$(T-38C) or $P_{luxI}$(C-77T). Also disclosed are an application of the auto-induction regulatory system based on quorum sensing in the automatic regulation of expression of a target gene of engineered *Escherichia coli*, as well as an application thereof in the preparation of alginate lyase and esterase. Further disclosed are a recombinant expression vector and a recombinant engineered bacterium comprising the auto-induction regulatory system based on quorum sensing.

5 Claims, 7 Drawing Sheets

Specification includes a Sequence Listing.

SEQUENCE LISTING

```
Sequence total quantity: 20
SEQ ID NO: 1              moltype = DNA  length = 145
FEATURE                   Location/Qualifiers
source                    1..145
                          mol_type = other DNA
                          organism = synthetic construct
SEQUENCE: 1
agtcctttga ttctaataaa tcgaattttt gtcacactat tgtatccctg ggaatacaat   60
tacttaacat aagcacctgt aggattgtcc aggtttacgc aataaaatgg tttgttatag  120
tcgaataaac gcaagggagg ttggt                                        145

SEQ ID NO: 2              moltype = DNA  length = 162
FEATURE                   Location/Qualifiers
source                    1..162
                          mol_type = other DNA
                          organism = synthetic construct
SEQUENCE: 2
caattccgac gtctaagaga ccattattat cgtgacatta acctataaga acaggcgtgt   60
cacgaggccc tttcgtcttc acctcgagtc cctatcagtg acagagattg acacccctat  120
cagtgataga gatactgagc acatcagcag gacgcactga cc                     162

SEQ ID NO: 3              moltype = DNA  length = 35
FEATURE                   Location/Qualifiers
source                    1..35
                          mol_type = other DNA
                          organism = synthetic construct
SEQUENCE: 3
ttgacggcta gctcagtcct aggtacagtg ctagc                              35

SEQ ID NO: 4              moltype = DNA  length = 145
FEATURE                   Location/Qualifiers
source                    1..145
                          mol_type = other DNA
                          organism = synthetic construct
SEQUENCE: 4
agtcctttga ttctaataaa tcgaattttt gtcacactat tgtatccctg ggaatacaat   60
tacttaacat aagcacctgt aggatcgtcc aggtttacgc aataaaatgg tttgttatag  120
tcgaataaac gcaagggagg ttggt                                        145

SEQ ID NO: 5              moltype = DNA  length = 145
FEATURE                   Location/Qualifiers
source                    1..145
                          mol_type = other DNA
                          organism = synthetic construct
SEQUENCE: 5
agtcctttga ttctaataaa tcgaattttt gtcacactat tgtatctctg ggaatacaat   60
```

```
tacttaacat aagcacctgt aggattgtcc aggtttacgc aataaaatgg tttgttatag  120
tcgaataaac gcaagggagg ttggt                                        145

SEQ ID NO: 6            moltype = DNA   length = 142
FEATURE                 Location/Qualifiers
source                  1..142
                        mol_type = other DNA
                        organism = synthetic construct
SEQUENCE: 6
agtcctttga ttctaataaa ttgaattttt gtcacactat tgtatcgctg ggaatacaat  60
tacttaacat aagcacctgt aggattgtcc aggtttacgc aaaatggttt gttatagtcg  120
aataaacgca agggaggttg gt                                           142

SEQ ID NO: 7            moltype = DNA   length = 145
FEATURE                 Location/Qualifiers
source                  1..145
                        mol_type = other DNA
                        organism = synthetic construct
SEQUENCE: 7
agtcctttga ttctaataga tcgaattttt gtcacactat tgtatcgctg ggaatacaat  60
tacttaacat aagcacctgt aggattgtcc aggtttacgc aataaaatgg tttgttatag  120
tctaataaac gcaagggagg ttggt                                        145

SEQ ID NO: 8            moltype = DNA   length = 145
FEATURE                 Location/Qualifiers
source                  1..145
                        mol_type = other DNA
                        organism = synthetic construct
SEQUENCE: 8
agtcctttga ttctaataaa tcgaattttt gtcacactat tgtatcgctg ggaatacaat  60
tacttaacat aagcaccggt aggatcgttc aggtttacgc aacaaatgg tttgttatag   120
tcgaataaac gcaagggagg ttggt                                        145

SEQ ID NO: 9            moltype = DNA   length = 573
FEATURE                 Location/Qualifiers
source                  1..573
                        mol_type = other DNA
                        organism = synthetic construct
SEQUENCE: 9
atgataaaaa aatcggactt tttgggcatt ccatcagagg agtatagagg tattcttagt  60
cttcgttatc aggtatttaa acgaagactg gagtgggact tggtaagtga ggataatctt  120
gaatcagatg aaatatgataa ctcaaatgca gaatatattt atgcttgtga tgatgcggaa 180
gaggtaaatg gctgttggcg tttgttacct acaacgggtg attacatgtt aaaaactgtt  240
tttcctgaat tgctcggaga tcaagtagcc ccaagagatc caaatatagt cgaattaagc  300
cgtttttgctg tgggaaaaaa tagctcaaaa ataaataact ctgctagtga ataacaatg   360
aaattgtttc aagctatata taaacacgca gttagtcaag gtattacaga atatgtaaca  420
gtaacatcaa tagcaataga gcgatttctg aaacgtatta aagttccttg tcatcgcatt  480
ggtgataagg agattcattt attaggtaat actagatctg ttgtattgtc tatgcctatt  540
aatgatcagt ttagaaaagc tgtatcaaat taa                               573

SEQ ID NO: 10           moltype = DNA   length = 753
FEATURE                 Location/Qualifiers
source                  1..753
                        mol_type = other DNA
                        organism = synthetic construct
SEQUENCE: 10
atgaacatta aaaatataaa tgctaatgag aagataattg ataaaattaa aacttgtaat  60
aataaaag atattaatca atgtttatct gaaatagcaa agataataca ttgtgaatat   120
tacctattcg ctattatcta tcctcactca ataattaaac ctgatgtttc aattatagat  180
aattaccctg aaaaatggcg taaatattat gatgatgccg gactactaga atatgaccct  240
gtagtcgatt actctaagtc ccatcattca ccaattaatt ggaacgtatt cgaaaaaaaa  300
acaataaaaa aagagtctcc gaatgtaata aaagaagcac aggaatcggg actcattact  360
ggatttagct ttccaattca tactgcaagt aatggttttg gaatgctcag ttttgctcat  420
tcagataaag atatttatac tgacagttta ttttacacg ctagtacaaa tgtaccatta   480
atgcttcctt ctttagtcga taattatcaa aaaataaata cgacacgtaa aaagtcagat  540
tctattttaa caaaaagaga aaagaatgc ttagcgtggg cgagtgaagg aaaaagtaca  600
tgggatattt caaaaatact tggctgcagt gagcgtactg tcacttttca tttaaccaat  660
actcaaatga aactcaatac aactaaccgc tgccaaagta tttctaaagc aattttaact  720
ggcgccatta attgtccata ccttaaaaat taa                               753

SEQ ID NO: 11           moltype = DNA   length = 717
FEATURE                 Location/Qualifiers
source                  1..717
                        mol_type = other DNA
                        organism = synthetic construct
SEQUENCE: 11
atggtgagca aggcgagga gctgttcacc ggggtggtgc ccatcctggt cgagctggac   60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
```

```
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaag       717
```

```
SEQ ID NO: 12          moltype = DNA  length = 1479
FEATURE                Location/Qualifiers
source                 1..1479
                       mol_type = other DNA
                       organism = synthetic construct
SEQUENCE: 12
atgaacagac caaggctcag cacctacgcc gcgatcaccg tcgcggccat cacgatcgcg     60
gccctcacca ccgcagcatc cgctctcgcc tccaccggcg atacgtcgtc gcgcaccccg    120
agcgggaact cgaccccaca ggccaacgcc accatcgtca acgtctcgtc gtcgacgcag    180
ttgaccaccg cgatggccaa cgccgtagcc ggcaaacga tcgtcctcgc caacggctcc     240
tactcgatcg gcaagctcaa cgccaagaac ggcacctcca gcgcacccat cacgatcatg    300
gccgcccaac agggcaaggc gatcatcacc ggagggcagc tcgaggttct cagctcgtcg    360
tacgtgacgt tctccgggct gaagtggacg aacagcaaca cgttgaagat caccagttcg    420
caccacatcc ggttaacccg caaccacttc cggctcaccg agtcgagctc gttgaagtgg    480
atcatcatcc agggagccaa cagccaccac aaccggatcg accacaacct gttcgaggag    540
aagcaccagc tcggcaactt catcaccatc gacgggtctt cgacccagca gtcgcagtac    600
gacctgatcg actacaacca ctttcgcaac atcggtccgc gcgccaccaa cgagatggag    660
gcgatccggg tcggctggag tgcgatctcc aagtcggacg ggttcaccac ggtcgagaac    720
aacctcttcg agaactgcga cggcgaccct gagatcgtct ccgtgaagag caacgccaac    780
accgtccggt acaacacctt ccggacatca cagggctcg tgtccctgcg cacacggcaac    840
cgcagccagg tccacggcaa cttcttcttc ggaggcggca agaccggcac cggcggcgtc    900
cgggtctacg gccaggacca caagatatac aacaaccact tcgaaggact gaccggcacc    960
ggctacgacg cggcgctgca actcgacggc ggggacgtcg acacctcagg cgcgctctcc   1020
tcgcactggc gggtgtaccg ggccacggca gtgcacaaca ccttcgtcaa caacgtctcg   1080
aacatcgaga tcggcgccaa ctacagtctc gccccggtcg acagcctggt cgccgacaac   1140
atcgtcgtcg gttcttccgg caagctcttc aacgagctga agatgcccaa gaacatgacg   1200
tacgcgggca acatcggctg gccgacgggt tccgccacca tcgggatcac caccggcgtc   1260
cgcaccgtga acccgctcct ggccaagcag ggtgaggtct accgcctcgg caccggtagc   1320
cccgcggtca acaccgcgtc gggtagctac agcttcctcg ccgatgacat ggacggtcag   1380
tcacgcagtg gaacggccga tgtcggagcg gacgaactgt ccaccggcac cgtggtccac   1440
aagccgctca actccgccga cgtcggaatc agcgcccccc                          1479
```

```
SEQ ID NO: 13          moltype = DNA  length = 1854
FEATURE                Location/Qualifiers
source                 1..1854
                       mol_type = other DNA
                       organism = synthetic construct
SEQUENCE: 13
atgctgctca gcaaacgccc gatccgctcc ctgatggcgg ccgcgatcgc gctggccgcg     60
gtaccggcca tggcaggcga atccccgtat tccagagccg tgttcttcgg tgacagcctc    120
accgatgccg gctatttccg cccgctgctg gatccgggcg tgcggccggt caccggccag    180
ttcaccacca acccgggctt ggtgtggtcg caacagttgg ccaattacta cggcctcgat    240
ggcacgccca acggtaatgg ccagaatggc gacaactacg ccgttggcgg cgcccgtgta    300
tcggtcgacg aagcgggtgg cctgggagcc attccgtcgc tgaagtcgca ggccgcccgt    360
taccttgccg caaatggcgg caaggctgac gccaatgccc tgtacaccgt ctggggcggt    420
gccaatgacc tgttcgcggc cacgcgcgca gcggccggcg gtgcatcgca ggcccaggtg    480
cagggcatca tcggggcagc agtcaccgac cagatcgccc tggtgggcgc actgaagcag    540
gccggggcac agtatgtgct ggtgccgaat ctgccggacg tgggcatcac tccgcagttc    600
cgcgccccca acgccgctgc cgccaccgcg ctgtcgccg gctacaacaa ggccctgtac    660
ggtggcctga gcaggcgggg catcgagttc attccgctcg acaccttcag catcctgcgc    720
gaggtgaccg ccaatccggc catgtatggc ttcaccaacg tcaccagcac ggcctgcaag    780
atcgatccga caattccac tgcgagcatc atcggctgca acccgaccag ctacgtcagc    840
ccggatgcgg ccaacaccta cctgttcgcc gacgcgtgc atccgaccac cgccggccat    900
cagctgctgg gccagtacgc ggtctcggtg ctggaaggcc gcgtctgca gcaggtgctg    960
agccactcgg cacagaccat cggccgctcg cgtgccgacc aggtcagcat gcacttgggt   1020
ggtcgcccgg ccgacggcct gtcctggtgg ggcggcgtgc gtggtgacct gcagcgctat   1080
gaccatgccg acctgtacga cggcctggcg ccggccggcc tgttcggtat cgactgggcg   1140
cgcgacggca tggtgttcgg cggcttcgcc ggcttcggcc gcctcaatgc cgacttcggc   1200
aacagccgtg gcgacttcac ccagaaggac accaccgccg tctgttcgc gggctggtac   1260
cacgaccgca tctgggtcaa tggccaggtc agctacacct ggttgtccta tgacgtgaac   1320
cgcaaggtcc agctgggtcc ggccaccccg gagcacggtg gttcgccgga cggcagcaac   1380
ctgactgctg ccctgaacgc cggttacgag ttcggcaccg aaggcggctt ccgccacggc   1440
ccgattgctt cggtgatctg gcagaaggtg aagatcgacg gttacaccga aagcgctgcg   1500
gccggaacg tggccaccgc actgggttac gaccgccaga acgttgattc gcactcggt   1560
cgcatcggct ggcaggcccg cttcgatggc ggcaccgtca gccgtacgc gcagttgacc   1620
tacgaccacg agttcgaaga caccaagcag gccagtgcct ggctgcagac cctgccggaa   1680
ctgggcagct atcgcgtgcc cggcctgaac ttcgacaaga actacgccac cgtggtgctg   1740
ggtgcccgta ccgagctgtt cggcctgcag agcaacttcg gcctgagcgc ttcggccggg   1800
cagaagcgtg cccaggacgc gacgctgttc gccaacttca gcggcagctt ctaa          1854
```

-continued

```
SEQ ID NO: 14                moltype = AA   length = 190
FEATURE                      Location/Qualifiers
source                       1..190
                             mol_type = protein
                             organism = synthetic construct
SEQUENCE: 14
MIKKSDFLGI PSEEYRGILS LRYQVFKRRL EWDLVSEDNL ESDEYDNSNA EYIYACDDAE    60
EVNGCWRLLP TTGDYMLKTV FPELLGDQVA PRDPNIVELS RFAVGKNSSK INNSASEITM   120
KLFQAIYKHA VSQGITEYVT VTSIAIERFL KRIKVPCHRI GDKEIHLLGN TRSVVLSMPI   180
NDQFRKAVSN                                                          190

SEQ ID NO: 15                moltype = AA   length = 250
FEATURE                      Location/Qualifiers
source                       1..250
                             mol_type = protein
                             organism = synthetic construct
SEQUENCE: 15
MNIKNINANE KIIDKIKTCN NNKDINQCLS EIAKIIHCEY YLFAIIYPHS IIKPDVSIID    60
NYPEKWRKYY DDAGLLEYDP VVDYSKSHHS PINWNVFEKK TIKKESPNVI KEAQESGLIT   120
GFSFPIHTAS NGFGMLSFAH SDKDIYTDSL FLHASTNVPL MLPSLVDNYQ KINTTRKKSD   180
SILTKREKEC LAWASEGKST WDISKILGCS ERTVTFHLTN TQMKLNTTNR CQSISKAILT   240
GAINCPYLKN                                                          250

SEQ ID NO: 16                moltype = AA   length = 253
FEATURE                      Location/Qualifiers
source                       1..253
                             mol_type = protein
                             organism = synthetic construct
SEQUENCE: 16
MVSKGEELFT GVVPILVELD GDVNGHKFSV SGEGEGDATY GKLTLKFICT TGKLPVPWPT    60
LVTTLTYGVQ CFSRYPDHMK QHDFFKSAMP EGYVQERTIF FKDDGNYKTR AEVKFEGDTL   120
VNRIELKGID FKEDGNILGH KLEYNYNSHN VYIMADKQKN GIKVNFKIRH NIEDGSVQLA   180
DHYQQNTPIG DGPVLLPDNH YLSTQSALSK DPNEKRDHMV LLEFVTAAGI TLGMDELYKG   240
NSITSYSIHY TKL                                                      253

SEQ ID NO: 17                moltype = AA   length = 493
FEATURE                      Location/Qualifiers
source                       1..493
                             mol_type = protein
                             organism = synthetic construct
SEQUENCE: 17
MNRPRLSTYA AITVAAITIA ALTTAASALA STGDTSSRTP SGNSTPQANA TIVNVSSSTQ    60
LTTAMANAVA GQTIVLANGS YSIGKLNAKN GTSSAPITIM AAQQGKAIIT GGQLEVLSSS   120
YVTFSGLKWT NSNTLKITSS HHIRLTRNHF RLTESSSLKW IIIQGANSHH NRIDHNLFEE   180
KHQLGNFITI DGSSTQQSQY DLIDYNHFRN IGPRATNEME AIRVGWSAIS KSDGFTTVEN   240
NLFENCDGDP EIVSVKSNAN TVRYNTFRTS QGSVSLRHGN RSQVHGNFFF GGGKTGTGGV   300
RVYGQDHKIY NNHFEGLTGT GYDAALQLDG GDVDTSGALS SHWRVYRATA VHNTFVNNVS   360
NIEIGANYSL APVDSLVADN IVVGSSGKLF NELKMPKNMT YAGNIGWPTG SATIGITTGV   420
RTVNPLLAKQ GEVYRLGTGS PAVNTASGSY SFLADDMDGQ SRSGTADVGA DELSTGTVVH   480
KPLNSADVGI SAP                                                      493

SEQ ID NO: 18                moltype = AA   length = 617
FEATURE                      Location/Qualifiers
source                       1..617
                             mol_type = protein
                             organism = synthetic construct
SEQUENCE: 18
MLLSKRPIRS LMAAAIALAA VPAMAGESPY SRAVFFGDSL TDAGYFRPLL DPGVRPVTGQ    60
FTTNPGLVWS QQLANYYGLD GTPNGNGQNG DNYAVGGARV SVDEAGGLGA IPSLKSQAAR   120
YLAANGGKAD ANALYTVWGG ANDLFAATRA AAGGASQAQV QGIIGAAVTD QIALVGALKQ   180
AGAQYVLVPN LPDVGITPQF RGPNAAAATA LSAGYNKALY GGLKQAGIEF IPLDTFSILR   240
EVTANPAMYG FTNVTSTACK IDPNNSTASI IGCNPTSYVS PDAANTYLFA DGVHPTTAGH   300
QLLGQYAVSV LEGPRLQQVL SHSAQTIGRS RADQVSMHLG GRPADGLSWW GGVRGDLQRY   360
DHADLYDGLA PAGLFGIDWA RDGMVFGGFA GFGRLNADFG NSRGDFTQKD TTAGLFAGWY   420
HDRIWVNGQV SYTWLSYDVN RKVQLGPATR EHGGSPDGSN LTAALNAGYE FGTEGGPRHG   480
PIASVIWQKV KIDGYTESAA AGTLATALGY DRQNVDSTVG RIGWQARFDG GTVKPYAQLT   540
YDHEFEDTKQ ASAWLQTLPE LGSYRVPGLN FDKNYATVVL GARTELFGLQ SNFGLSASAG   600
QKRAQDATLF ANFSGSF                                                  617

SEQ ID NO: 19                moltype = DNA   length = 3698
FEATURE                      Location/Qualifiers
source                       1..3698
                             mol_type = other DNA
                             organism = synthetic construct
SEQUENCE: 19
caaaaaaccc ctcaagaccc gtttagaggc cccaaggggt tatgctagtt attgctcagc    60
ggtggcagca gccaactcag cttcctttcg ggctttgtta gcagccggat ctcagtggtg   120
gtggtggtgg tgctcgagtg cggccgcaag cttggggggcg ctgattccga cgtcggcgga   180
```

```
gttgagcggc ttgtggacca cggtgccggt ggacagttcg tccgctccga catcggccgt   240
tccactgcgt gactgaccgt ccatgtcatc ggcgaggaag ctgtagctac ccgacgcggt   300
gttcaccgcg gggctaccgg tgccgaggcg gtagacctca ccctgcttgg ccaggagcgg   360
gttcacggtg cggacgccgg tggtgatccc gatggtggcg gaacccgtcg gccagccgat   420
gttgcccgcg tacgtcatgt tcttgggcat cttcagctcg ttgaagagct tgccggaaga   480
accgacgacg atgttgtcgg cgaccaggct gtcgaccggg gcgagactgt agttggcgcc   540
gatctcgatg ttcgagacgt tgttgacgaa ggtgttgtgc actgccgtgg cccggtacac   600
ccgccagtgc gaggagagcg cgcctgaggt gtcgacgtcc ccgccgtcga gttgcagcgc   660
cgcgtcgtag ccggtgccgg tcagtccttc gaagtggttg ttgtatatct tgtggtcctg   720
gccgtagacc cggacgccgc cggtgccggt cttgccgcct ccgaagaaga agttgccgtg   780
gacctggctg cggttgccgt ggcgcaggga caccgagccc tgtgatgtcc ggaaggtgtt   840
gtaccggacg gtgttggcgt tgctcttcac ggagacgatc tcagggtcgc cgtcgcagtt   900
ctcgaagagg ttgttctcga ccgtggtgaa cccgtccgac ttggagatcg cactccagcc   960
gacccggatc gcctccatct cgttggtggc gcgcggaacg atgttgcgaa agtggttgta   1020
gtcgatcagg tcgtactgcg actgctgggc cgaagacccg tcgatggtga tgaagttgcc   1080
gagctggtgc ttctcctcga acaggttgtg gtcgatccgg ttgtggtggc tgttggctcc   1140
ctggatgatg atccacttca acgagctcga ctcggtgagc cggaagtggt tgcgggttaa   1200
ccggatgtgg tgcgaactgg tgatcttcaa cgtgttgctg ttcgtccact tcagcccgga   1260
gaacgtcacg tacgacgagc tgagaacctc gagctgccct ccggtgatga tcgccttgcc   1320
ctgttgggcg gccatgatcg tgatgggtgc gctggaggtg ccgttcttgg cgttgagctt   1380
gccgatcgag taggagccgt tggcgaggac gatcgtttgg ccggctacgg cgttggccat   1440
cgcggtggtc aactgcgtcg acgacgagac gttgacgatg gtggcgttgg cctgtggggt   1500
cgagttcccg ctcggggtgc gcgacgacgt atcgccggtg gaggcgagag cggatgctgc   1560
ggtggtgagg gccgcgatcg tgatggccgc gacggtgatc gcggcgtagg tgctgagcct   1620
tggtctgttc atgaattcgg atccgcgacc catttgctgt ccaccagtca tgctagccat   1680
atggctgccg cgcggcacca ggccgctgct gtgatgatga tgatgatgc tgctgcccat   1740
ggtatatctc cttcttaaag ttaaacaaaa ttatttctag aggggaattg ttatccgctc   1800
acaattcacc aacctccctt gcgtttattc gactataaca aaccatttta ttgcgtaaac   1860
ctggacaatc ctacaggtgc ttatgttaag taattgtatt cccagggata caatagtgtg   1920
acaaaaattc gatttattag aatcaaagga ctatttcgcg ggatcgagat ctcgatcctc   1980
tacgccggac gcatcgtggc cggcatcacc ggcgccacag gtgcggttgc tggcgcctat   2040
atcgccgaca tcaccgatgg ggaagatcgg gctcgccact tcgggctcat gagcgcttgt   2100
ttcggcgtgg gtatggtggc aggccccgtg gcccaaaaaa cccctcaaga cccgtttaga   2160
ggccccaagg ggttatgcta gttaattttt aaggtatgga caattaatgg cgccagttaa   2220
aattgcttta gaaatacttt ggcagcggtt agttgtattg agtttcattt gagtattggt   2280
taaatgaaaa gtgacagtac gctcactgca gccaagtatt tttgaaatat cccatgtact   2340
ttttccttca ctcgcccacg ctaagcattc ttttctctt tttgttaaaa tagaatctga   2400
cttttttacgt gtcgtattta ttttttgata attatcgact aaagaaggaa gcattaatgg   2460
tacatttgta ctagcgtgta aaaataaact gtcagtataa atatctttat ctgaatgagc   2520
aaaactgagc attccaaaac cattacttgc agtatgaatt ggaaagctaa atccagtaat   2580
gagtcccgat tcctgtgctt cttttattac attcggagac tctttttta ttgtttttt   2640
ttcgaatacg ttccaattaa ttggtgaatg atgggactta gagtaatcga ctacagggtc   2700
atattctagt agtccggcat catcataata tttacgccat ttttcagggt aattatctat   2760
aattgaaaca tcaggtttaa ttattgagtg aggatagata atagcgaata ggtaatattc   2820
acaatgtatt atctttgcta tttcagataa acattgatta atatctttat tattattaca   2880
agtttttaatt ttatcaatta tcttctcatt agcatttata tttttaatgt tcattctcct   2940
tcttaaagtt aaacaaatta atttgataca gcttttctaa actgatcatt aataggcata   3000
gacaatacaa cagatctagt attacctaat aaatgaatct ccttatcacc aatgcgatga   3060
caaggaactt taatacgttt cagaaatcgc tctattgcta ttgatgttac tgttacatat   3120
tctgtaatac cttgactaac tgcgtgttta tatatagctt gaaacaattt cattgttatt   3180
tcactagcag agttatttat ttttgagcta tttttccca cagcaaaacg gcttaattcg   3240
actatatttg gatctcttgg ggctacttga tctccgagca attcaggaaa aacagttttt   3300
aacatgtaat cacccgttgt aggtaacaaa cgccaacagc catttacctc ttccgcatca   3360
tcacaagcat aaatatattc tgcatttgag ttatcatatt catctgattc aagattatcc   3420
tcacttacca agtcccactc cagtcttcgt ttaaatacct gataacgaag actaagaata   3480
cctctatact cctctgatgg aatgcccaaa aagtccgatt tttttatcat tctccttctt   3540
aaagttaaac aaaagtcctt tgattctaat aaatcgaatt tttgtcacac tattgtatcc   3600
ctgggaatac aattacttaa cataagcacc tgtaggattg tccaggtta cgcaataaaa   3660
tggtttgtta tagtcgaata aacgcaaggg aggttggt   3698
```

```
SEQ ID NO: 20              moltype = DNA   length = 4070
FEATURE                    Location/Qualifiers
source                     1..4070
                           mol_type = other DNA
                           organism = synthetic construct
SEQUENCE: 20
caaaaaaccc ctcaagaccc gtttagaggc cccaaggggt tatgctagtt attgctcagc   60
ggtggcagca gccaactcag cttccttcg ggctttgtta gcagccggat ctcagtggtg   120
gtggtggtgg tgctcgagtg cggccgcaag cttgaagctg ccgctgaagc tggcgaacag   180
cgtcgcgtcc tgggcacgct tctgcccggc cgaagcgctc aggccgaagt tgctctgcag   240
gccgaacagc tcggtacggg cacccagcac cacggtggcg tagttcttgt cgaagttcag   300
gccgggcacg cgatagctgc ccagttccgg cagggtctgc agccaggcac tggcctgctt   360
ggtgtcttcg aactcgtggt cgtaggtcaa ctgcgcgtac ggcttgacgg tgccgccatc   420
gaagcggtac tgcgaccgac tgcgaccgac ggtgaatca acgttctggc ggtcgtaacc   480
cagtgcggtg gccagggtgc cggccgcagc gctttcggtg taaccgtcga tcttcacctt   540
ctgccagatc accgaagcaa tcgggccgtg cgggaagccg ccttcggtgc cgaactcgta   600
accgcgttag agggcagcag tcaggttgct gccgtccggc gaaccaccgt gctcgcgggt   660
ggccggaccc agctggacct tgcggttcac gtcataggac aaccaggtgt agctgacctg   720
gccattgacc cagatgcggt cgtggtacca gcccgcgaac agaccggcgg tggtgtcctt   780
```

-continued

```
ctgggtgaag tcgccacggc tgttgccgaa gtcggcattg aggcggccga agccggcgaa   840
gccgccgaac accatgccgt cgcgcgccca gtcgataccg aacaggccgg ccggcgccag   900
gccgtcgtac aggtcggcat ggtcatagcg ctgcaggtca ccacgcacgc cgcccacca    960
ggacaggccg tcggccgggc gaccacccaa gtgcatgctg acctggtcgg cacgcgagcg   1020
gccgatggtc tgtgccgagt ggctcagcac ctgctgcaga cgcgggcctt ccagcaccga   1080
gaccgcgtac tggcccagca gctgatggcc ggcggtggtc ggatgcacgc cgtcggcgaa   1140
caggtaggtg ttggccgcat ccgggctgac gtagctggtc gggttgcagc cgatgatgct   1200
cgcagtggaa ttgttcggat cgatcttgca ggccgtgctg gtgacgttgg tgaagccata   1260
catggccgga ttggcggtca cctcgcgcag gatgctgaag gtgtcgagcg gaatgaactc   1320
gatgcccgcc tgcttcaggc caccgtacag ggccttgttg tagccggccg acagcgcggt   1380
ggcggcagcg gcgttggggc cgcggaactg cggagtgatg cccacgtccg gcagattcgg   1440
caccagcaca tactgtgccc cggcctgctt cagtgcgccc accagggcga tctggtcggt   1500
gactgctgcc ccgatgatgc cctgcacctg ggcctgcgat gcaccgccgg ccgctgcgcg   1560
cgtggccgcg aacaggtcat tggcaccgcc ccagacggtg tacagggcat tggcgtcagc   1620
cttgccgcca tttgcggcaa ggtaacgggc ggcctgcgac ttcagcgacg gaatggctcc   1680
caggccaccc gcttcgtcga ccgatacacg ggcgccgcca acggcgtagt tgtcgccatt   1740
ctggccatta ccgttgggcg tgccatcgag gccgtagtaa ttggccaact gttgcgacca   1800
caccaagccc gggttggtgg tgaactggcc ggtgaccggc cgcaccgcccg gatccagcag   1860
cgggcggaaa tagccggcat cggtgaggct gtcaccgaag aacacggctc tggaatacgg   1920
ggattcgcct gccatggccg gtaccgcggc cagcgcgatc gcggccgcca tcagggagcg   1980
gatcgggcgt ttgctgagca gcatgaattc ggatccgcga cccatttgct gtccaccagt   2040
catgctagcc atatggctgc cgcgcggcac caggccgctg ctgtgatgat gatgatgatg   2100
gctgctgccc atggtatatc tccttcttaa agttaaacaa aattatttct agaggggaat   2160
tgttatccgc tcacaattca ccaacctccc ttgcgtttat tcgactataa caaaccattt   2220
tattgcgtaa acctggacaa tcctacaggt gcttatgtta agtaattgta ttcccaggga   2280
tacaatagtg tgacaaaaat tcgatttatt agaatcaaag gactatttcg cgggatcgag   2340
atctcgatcc tctacgccgg acgcatcgtg gccggcatca ccggcgccac aggtgcggtt   2400
gctggcgcct atatcgccga catcaccgat ggggaagatc gggctcgcca cttcgggctc   2460
atgagcgctt gtttcggcgt gggtatggtg gcaggccccg tggcccaaaa aacccctcaa   2520
gacccgttta gaggccccaa ggggttatgc tagttaattt ttaaggtatg gacaattaat   2580
ggcgccagtt aaaattgctt tagaaatact ttggcagcgg ttagttgtat tgagtttcat   2640
ttgagtattg gttaaatgaa aagtgacagt acgctcactg cagccaagta tttttgaaat   2700
atcccatgta cttttttcctt cactcgccca cgctaagcat tcttttttctc tttttgttaa   2760
aatagaatct gactttttac gtgtcgtatt tattttttga taattatcga ctaaagaagg   2820
aagcattaat ggtacatttg tactagcgtg taaaaataaa ctgtcagtat aaatatcttt   2880
atctgaatga gcaaaactga gcattccaaa accattactt gcagtatgaa ttggaaagct   2940
aaatccagta atgagtcccg attcctgtgc ttcttttatt acattcggag actctttttt   3000
tattgttttt ttttcgaata cgttccaatt aattggtgaa tgatgggact tagagtaatc   3060
gactacaggg tcatattcta gtagtccggc atcatcataa tatttacgcc atttttcagg   3120
gtaattatct ataattgaaa catcaggttt aattattgag tgaggataga taatagcgaa   3180
taggtaatat tcacaatgta ttatctttgc tatttcagat aaacattgat taatatcttt   3240
attattatta caagttttaa ttttatcaat tatcttctca ttagcattta tatttttaat   3300
gttcattctc cttcttaaag ttaaacaaat taatttgata cagctttttct aaactgatca   3360
ttaataggca tagacaatac aacagatcta gtattaccta ataaatgaat ctccttatca   3420
ccaatgcgat gacaaggaac tttaatacgt ttcagaaatc gctctattgc tattgatgtt   3480
actgttacat attctgtaat accttgacta actgcgtgtt tatatatagc ttgaaacaat   3540
ttcattgtta tttcactagc agagttattt attttttgagc tatttttttcc cacagcaaaa   3600
cggcttaatt cgactatatt tggatctctt ggggctactt gatctccgag caattcagga   3660
aaaacagttt ttaacatgta atcacccgtt gtaggtaaca aacgccaaca gccatttacc   3720
tcttccgcat catcacaagc ataaatatat tctgcatttg agttatcata ttcatctgat   3780
tcaagattat cctcacttac caagtcccac tccagtcttc gtttaaatac ctgataacga   3840
agactaagaa tacctctata ctcctctgat ggaatgccca aaaagtccga ttttttttatc   3900
attctccttc ttaaagttaa acaaaagtcc tttgattcta ataaatcgaa tttttgtcac   3960
actattgtat ccctgggaat acaattactt aacataagca cctgtaggat tgtccaggtt   4020
tacgcaataa aatggtttgt tatagtcgaa taaacgcaag ggaggttggt              4070
```

AUTO-INDUCTION REGULATORY SYSTEM BASED ON QUORUM SENSING AND APPLICATION THEREOF

TECHNICAL FIELD

The present disclosure relates to an auto-induction regulatory system based on quorum sensing and an application thereof, belonging to the technical field of genetic engineering.

REFERENCE TO SEQUENCE LISTING

The substitute sequence listing is submitted as a XML file filed via EFS-Web, with a file name of "Substitute_Sequence_Listing.XML", a creation date of Jul. 1, 2022, and a size of 34,389 bytes. The substitute sequence Listing filed via EFS-Web is a part of the specification and is incorporated in its entirety by reference herein.

BACKGROUND ART

*Escherichia coli* is a commonly used strain in genetic engineering, and is widely used in the enzyme expression, metabolic engineering, synthesis of high-value compounds, etc. Traditional genetic modification strategies are mainly static regulation strategies such as overexpression and knockout of genes. These strategies can improve the production performance of strains to a certain extent, but cannot balance the growth of strains and the synthesis of target products. However, the inducible promoters commonly used in *Escherichia coli* can achieve a certain degree of balance between growth and production, but there are certain limits. In addition, the inducers are toxic, expensive, and not suitable for mass production. In the field of dynamic regulation, there is a lack of effective biosensors. Therefore, it is necessary to develop dynamic regulatory elements with broad adaptability so as to adapt to the industrial production of different enzymes.

Quorum sensing is a system in microorganisms that regulates the expression of related genes as the cell density increases, and its autoinducer is a signaling molecule secreted by the microorganism itself. In different microorganisms, the quorum sensing systems are different, and the synthesized and secreted autoinducers are also different. The autoinducers are mainly divided into three types: Gram-negative bacteria-synthesized acyl-homoserine lactones (AHLs), Gram-positive bacteria-synthesized auto-inducing peptide (AIP) as well as AI-2 for the communication between Gram-positive bacteria and Gram-negative bacteria. Wherein, the LuxI/LuxR system existed in the Gram-negative bacteria is mostly studied, and the principle of such a quorum sensing system is as shown in FIG. 1A-B. With the growth of microorganisms, the cell density increases continuously, the signaling molecule AHLs synthesized by the signaling molecule synthetase LuxI increases continuously, and the AHLs enters and leaves the cells freely along the concentration gradient and accumulates outside the cells. After reaching a certain threshold, the concentration of AHLs in the cytoplasm will increase and they may further bind to the signaling molecule binding protein LuxR, thereby forming a dimer LuxR-AHL, which can activate the transcription of related genes as the activator of the promoter $P_{luxI}$.

The expression of related genes can be automatically regulated by applying the quorum sensing system in the expression of enzymes without additionally adding inducers, which is economic and feasible for large-scale industrial application. Currently, the quorum sensing system has been widely used in the fields of metabolic regulation of *Escherichia coli* and *Bacillus subtilis*, but its application is limited due to that the quorum sensing system may activate the expression of target genes at a specific threshold. Therefore, it is necessary to modify the critical elements of the quorum sensing system to enrich the dynamic regulatory element library of the quorum sensing system, so that the quorum sensing system can be better applied in the regulation of enzyme expression and metabolic engineering.

SUMMARY

In view of the above prior art, the present disclosure constructs an auto-induction dynamic regulatory system based on LuxI/LuxR quorum sensing, employs promoter engineering to modify the promoters, and selects a system suitable to different enzymes for expression and high-density fermentation.

The present disclosure is realized through the following technical schemes:

An auto-induction regulatory system based on quorum sensing, including luxI, luxR and egfp, wherein, the promoter for controlling the expression of luxI and luxR is selected from $P_{luxI}$, $P_{BB}$ or $P_{J23100}$; the promoter for controlling the expression of egfp is selected from $P_{luxI}$, $P_{luxI}$(T-38C) or $P_{luxI}$(C-77T).

Preferably, the auto-induction regulatory system based on quorum sensing is selected from one of the following:

① including $P_{luxI}$, luxI, luxR, $P_{luxI}$ and egfp connected in sequence.

② including $P_{BB}$, luxI, luxR, $P_{luxI}$ and egfp connected in sequence.

③ including $P_{J23100}$, luxI, luxR, $P_{luxI}$ and egfp connected in sequence.

④ including $P_{J23100}$, luxI, luxR, $P_{luxI}$(T-38C) and egfp connected in sequence.

⑤ including $P_{J23100}$, luxI, luxR, $P_{luxI}$(C-77T) and egfp connected in sequence.

The nucleotide sequence of the $P_{luxI}$ is as set forth in SEQ ID NO 1.

The nucleotide sequence of the $P_{BB}$ is as set forth in SEQ ID NO 2.

The nucleotide sequence of the $P_{J23100}$ is as set forth in SEQ ID NO 3.

The nucleotide sequence of the $P_{luxI}$(T-38C) is as set forth in SEQ ID NO 4.

The nucleotide sequence of the $P_{luxI}$(C-77T) is as set forth in SEQ ID NO 5.

The nucleotide sequences of the luxI, luxR and egfp are as set forth in SEQ ID NO 9, SEQ ID NO 10, SEQ ID NO 11, and the corresponding amino acid sequences are as set forth in SEQ ID NO 14, SEQ ID NO 15, SEQ ID NO 16.

An application of the auto-induction regulatory system based on quorum sensing in the automatic regulation of expression of a target gene in engineered *Escherichia coli*. The target gene is selected from an alginate lyase gene, and an esterase gene.

An application of the auto-induction regulatory system based on quorum sensing in the preparation of alginate lyase and esterase.

An engineered bacterium containing the above auto-induction regulatory system based on quorum sensing. The host of the engineered bacterium is *Escherichia coli*.

A recombinant expression vector including alginate lyase gene, whose structure is $P_{luxI}$-luxIR-$P_{luxI}$(T-38C)-al493.

A recombinant engineered bacterium expressing alginate lyase, which contains the above recombinant expression vector in its genome. The host of the engineered bacterium is *Escherichia coli*.

An application of the above recombinant expression vector and the recombinant engineered bacterium in the preparation of alginate lyase.

A recombinant expression vector containing esterase gene, whose structure is $P_{luxI}$-luxIR-$P_{luxI}$(C-77T)-est7.

A recombinant engineered bacterium expressing esterase, which contains the above recombinant expression vector in its genome. The host of the engineered bacterium is *Escherichia coli*.

An application of the above recombinant expression vector and the recombinant engineered bacterium in the preparation of esterase.

The present disclosure firstly constructs a quorum sensing system in *Escherichia coli*, and verifies that the quorum sensing system can function stably in *Escherichia coli*: secondly, replaces the promoter Plus for controlling the expression of luxI and luxR with constitutive promoters $P_{BB}$ and $P_{J23100}$, finding that $P_{J23100}$ has the best effect of regulating the expression. The present disclosure also employs a method of multiple rounds of error-prone PCR to mutate the promoter Plus, and uses green fluorescent protein as a reporter protein to obtain mutants through plate culture screening and liquid culture screening, so as to construct a promoter mutant library. The mutants obtained above are characterized one by one to determine the growth curve and the fluorescence expression of the mutants. The mutants exhibit different characteristics, which can meet multiple requirements for heterologous expression. From them, two representative mutant promoters are selected, Plus (T-38C), the promoter with the highest fluorescence intensity and increased fluorescence intensity per cell, and $P_{luxI}$(C-77T), the promoter with increased cell density during the regulation of expression. In the present disclosure, the screened promoters PluxI(T-38C), PluxI(C-77T) and the original promoter $P_{luxI}$ are constructed into a complete quorum sensing system, which is applied in the expression of alginate lyase and esterase, and with the strains expressing the two proteins under the induction of the inducible promoter T7 as a control, the bacterial density and enzymatic activity are determined by interval sampling, finding that the promoter with the highest enzymatic activity in the expression of alginate lyase is $P_{luxI}$(T-38C), the optimal promoter for the expression of esterase is $P_{luxI}$(C-77T), and their enzymatic activity are both comparable to that of the control group. Moreover, the alginate lyase activity of the high-density fermentation strain PJ23100-luxIR-$P_{luxI}$(T-38C)-al493 is 31.88 U/mL, which is 4.33 times that of the T7 promoter in the control group.

In the present disclosure, the promoters in the quorum sensing system are modified and screened to construct an auto-induction regulatory system suitable for expression of different enzymes. This system can realize high-efficient protein expression without the need of additionally adding inducers, for which the expression level in batch fermentation is comparable to that of the T7 promoter, and the expression level in high-density fermentation is significantly better than that of the T7 promoter.

Various terms and phrases used in the present disclosure have the general meaning known to those skilled in the art.

BRIEF DESCRIPTION OF THE DRAWINGS

FIG. 1B, high cell density.

FIG. 2B, $P_{luxI}$-luxIR-$P_{luxI}$-egfp; FIG. 2C, $P_{BB}$-luxIR-$P_{luxI}$-egfp; FIG. 2D, $P_{J23100}$-luxIR-$P_{luxI}$-egfp.

FIG. 3B, OD600 at which fluorescence intensity reaches the highest; FIG. 3C, the highest fluorescence intensity; FIG. 3D, highest fluorescence intensity per cell density.

FIG. 4B, esterase Est7.

FIG. 5B, T7-al493.

DETAILED DESCRIPTION OF THE EMBODIMENTS

The present disclosure will be further illustrated in conjunction with the embodiments below. However, the scope of the present disclosure is not limited to the following embodiments. It should be understood by those skilled in the art that various changes and modifications can be made to the present disclosure without deviating from the spirit and scope of the present disclosure.

The instruments, reagents, materials, etc. involved in the following embodiments, unless otherwise specified, are all conventional instruments, reagents, materials, etc. available in the prior art, which can be obtained through regular commercial channels. The experimental methods, detection methods, etc. involved in the following embodiments, unless otherwise specified, are conventional experimental methods, detection methods, etc. available in the prior art.

Embodiment 1 Construction of an Auto-Induction Dynamic Regulatory System

Figure 1A:
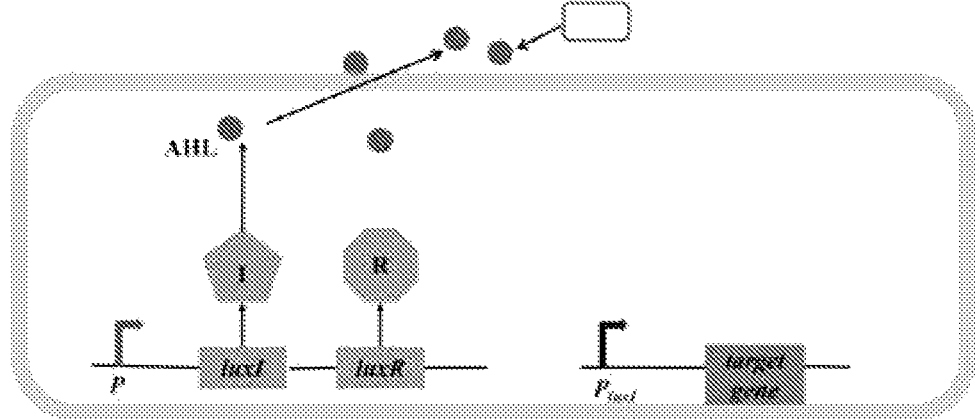
FIG. 1A-B are schematic diagrams showing the principle of a LuxI/LuxR quorum sensing system, wherein, FIG. 1A, low cell density.
Figure 1B:
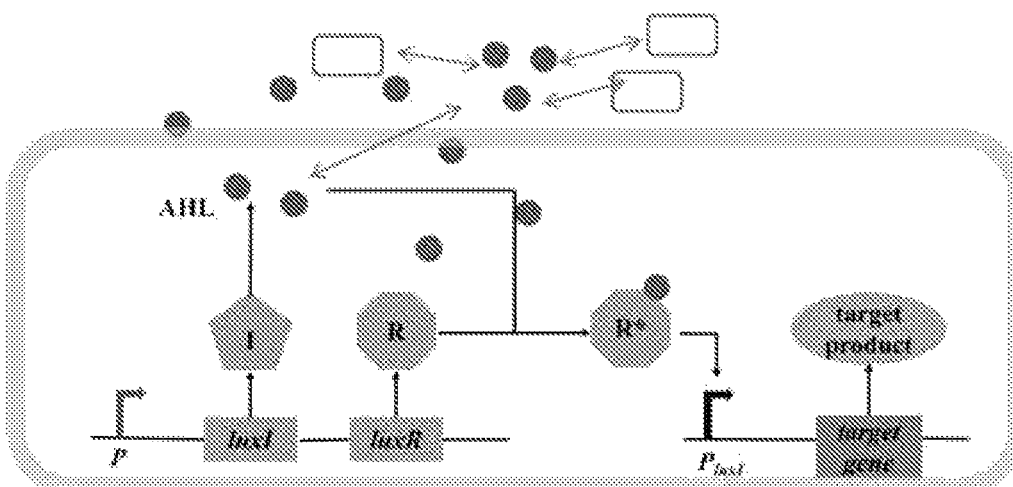
Figure 2A:
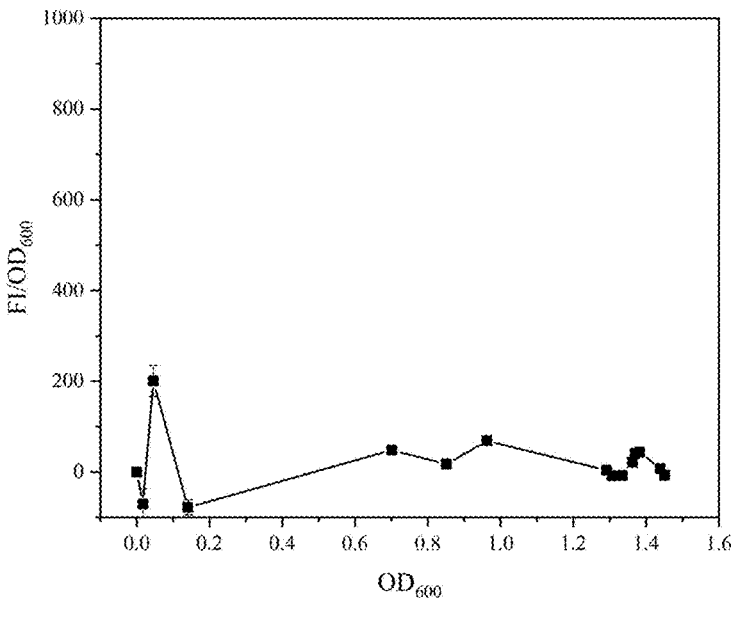
FIG. 2A-D are diagrams characterizing a quorum sensing system that regulates luxIR with different promoters, wherein, FIG. 2A, $P_{luxI}$-egfp.
Figure 2A:
Figure 2B:
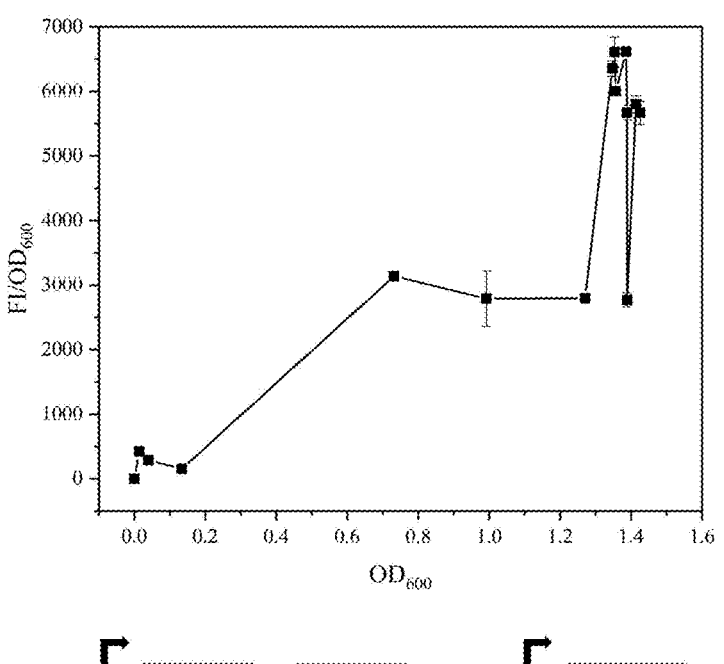
Figure 2C:
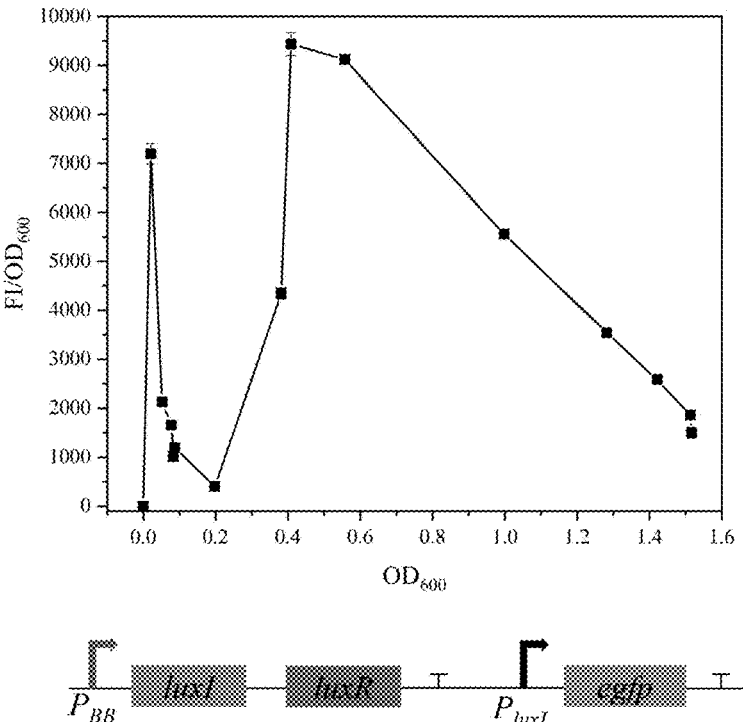
Figure 2D:
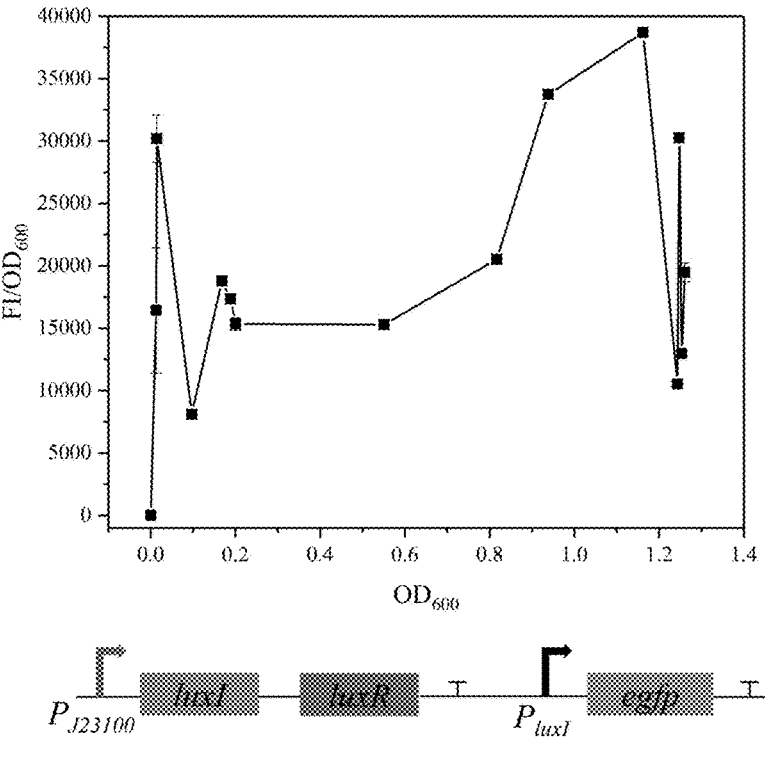
Figure 3A:
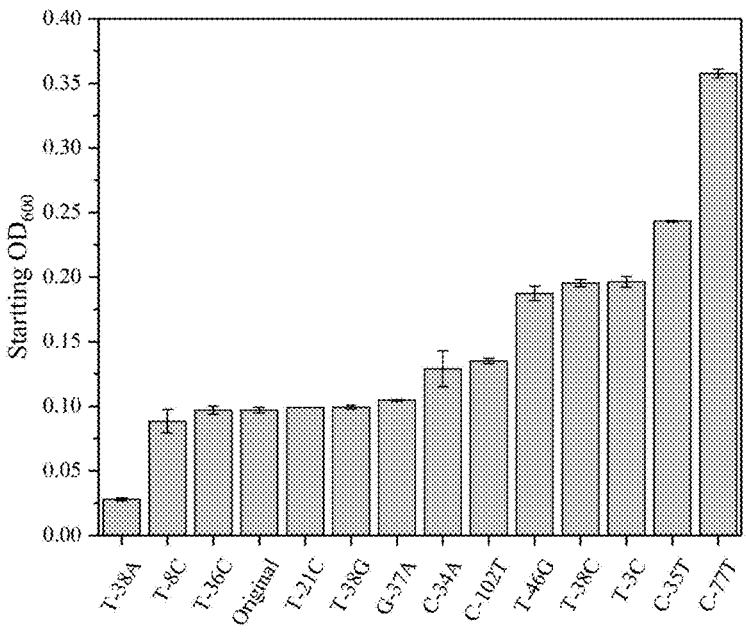
FIG. 3A-D are summarized schematic diagrams characterizing $P_{luxI}$ quorum sensing-mutated strains, wherein, FIG. 3A, initial OD600 at which fluorescence intensity starts to increase.
Figure 3B:
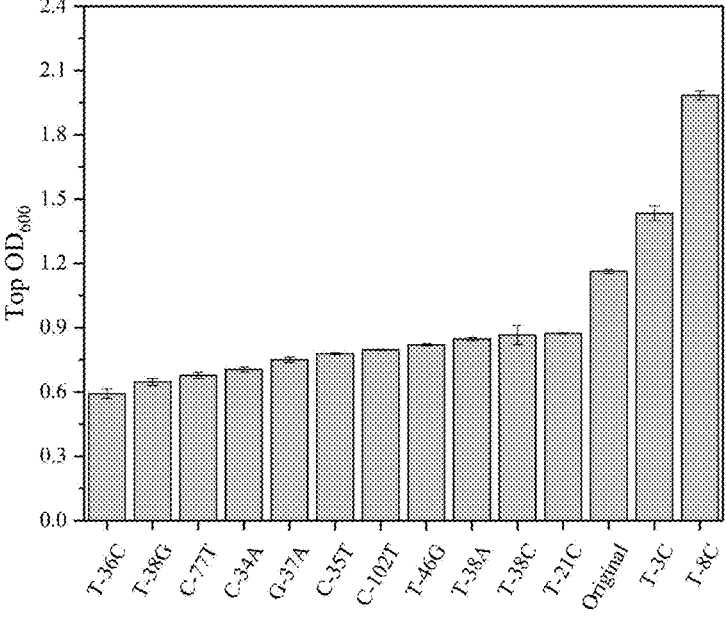
Figure 3C:
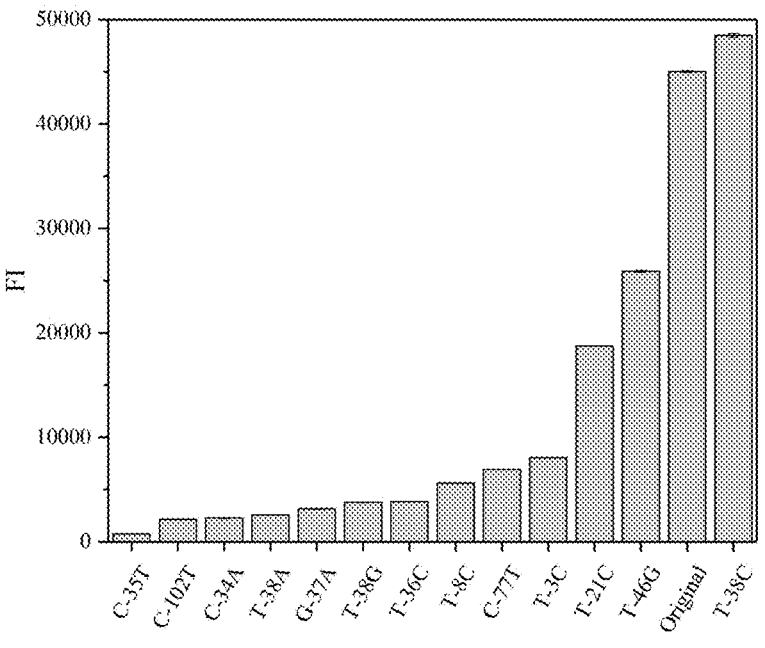
Figure 3D:
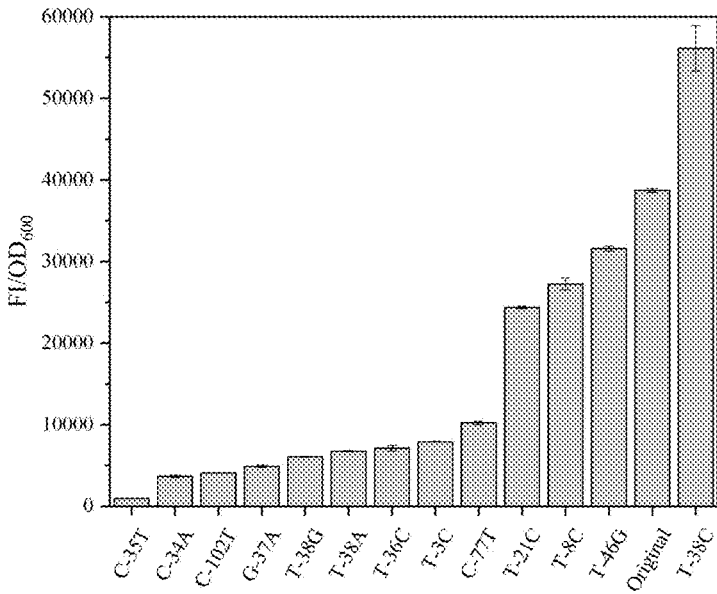

With plasmid pET28a as the original plasmid, egfp, $P_{luxI}$, luxI and luxR fragments were successively recombined with a plasmid vector by a seamless splicing method. Engineered strains were obtained with *Escherichia coli* BL21 (DE3) as the host. After cultivation with $P_{luxI}$-egfp strains as control, OD600 and fluorescence intensity (Ex: 488 nm; Em: 530 nm) were determined. As shown in the results of FIG. 2A and FIG. 2B, in the case of the promoter Plus alone, the highest value of the unit fluorescence intensity was about 200 au, while in strains containing a complete quorum sensing system, the unit fluorescence intensity was about 7000 au, suggesting that the auto-induction dynamic regulatory system was constructed successfully, which could function in *Escherichia coli*, and luxI and luxR were key components of the auto-induction dynamic regulatory system.

Embodiment 2 Optimization of the Regulatory luxIR Promoter

The regulatory promoter Plus of luxIR was replaced with constitutive promoters $P_{BB}$ and $P_{J23100}$, cultured with *E. coli* BL21 (DE3) as the expression host, and determined for OD600 and fluorescence intensity. By comparing the unit fluorescence intensity, with the results shown in FIG. 2A-D, it was indicated that the unit fluorescence intensity of strains with promoters $P_{luxI}$ and $P_{BB}$ were about 7000 au and 9500 au respectively, while the unit fluorescence intensity of the strain regulated by $P_{J23100}$ could reach 38000 au, and fluorescent protein with high expression level could be obtained under the regulation of $P_{J23100}$, so $P_{J23100}$ had the best regulation effect.

Embodiment 3 Construction. Screening and Characterization of PluxI Mutant Library With plasmid $P_{J23100}$-luxIR-$P_{luxI}$-egfp as the original plasmid. $P_{luxI}$ was randomly mutated using a controlled error-prone PCR kit in a manner of multiple rounds of error-prone PCR. Preliminary screening was performed by observing the fluorescence intensity of the strains and the time of fluorescence generation through plate culture, and the screened strains were cultured in liquid, and the strains that did not generate fluorescence were removed by further screening. The obtained strains were sequenced to identify the mutation sites. After screening and sequencing, 13 single-site mutants and 3 multi-site mutants were obtained (the 3 multi-site mutants were deletion of three bases in Q1, G-6T/A-105G, T-21C/C-35T/T-38C/T-46G, respectively, whose nucleotide sequences were as set forth in SEQ ID NOs 6-8), wherein, all the multi-site mutants did not generate fluorescence, and the single-site mutants were determined for growth curve and fluorescence intensity. With the initial OD600 at which the fluorescence expression was regulated, the OD600 at which FI reached the highest, the highest FI and the highest FI/OD600 as indicators, the data were summarized as shown in Table 1 and FIG. 3A-D, thereby identifying two representative promoters $P_{luxI}$(T-38C) and $P_{luxI}$(C-77T).

TABLE 1

Summary of characterization data of single-site
mutants of $P_{luxI}$, the promoter in quorum sensing

| Promoter Mutation | Initial OD600 for regulation of expression | OD600 at the highest FI | Highest FI | Final FI/OD600 |
|---|---|---|---|---|
| Control | 0.097 | 1.162 | 45024.2 | 38699.8 |
| T-3C | 0.196 | 1.434 | 8049.3 | 7908.0 |
| T-8C | 0.088 | 1.984 | 5616.5 | 27254.8 |
| T-21C | 0.099 | 0.874 | 18751.3 | 24369.8 |
| C-34A | 0.129 | 0.705 | 2275.4 | 3672.6 |
| C-35T | 0.243 | 0.779 | 769.4 | 987.7 |
| T-36C | 0.097 | 0.592 | 3839.4 | 7122.7 |
| G-37A | 0.105 | 0.750 | 3156.5 | 4889.4 |
| T-38A | 0.028 | 0.847 | 2580.5 | 6740.8 |
| T-38C | 0.195 | 0.868 | 48493.6 | 56115.2 |
| T-38G | 0.099 | 0.647 | 3771.8 | 6055.9 |
| T-46G | 0.187 | 0.820 | 25883.8 | 31579.7 |
| C-77T | 0.358 | 0.678 | 6933.5 | 10234.3 |
| C-102T | 0.135 | 0.796 | 2154.0 | 4089.9 |

Embodiment 4 Application of $P_{luxI}$ Mutants in the Expression of Alginate Lyase AL493

The quorum sensing system with three promoters $P_{luxI}$, $P_{luxI}$(T-38C) and $P_{luxI}$(C-77T) was applied in the expression of alginate lyase AL493 (whose nucleotide sequence was set forth in SEQ ID NO 12, and whose amino acid sequence was set forth in SEQ ID NO 17), so as to construct strains PluxI-luxIR-PluxI-al493 (the complete sequence of the constructed related gene was set forth in SEQ ID NO 19), $P_{J23100}$-luxIR-$P_{luxI}$(T-38C)-al493 and $P_{J23100}$-luxIR-$P_{luxI}$

6

(C-77T)-al493, while using the fermentation culture results of T7-al493 as control. The strains regulated by the quorum sensing system were cultured at 20° C., while the strains regulated by T7 promoter needed to be firstly cultured at 37° C. to an OD600 of 0.6 and induced by adding IPTG with a final concentration of 0.5% 0, and then the culture temperature was changed to 20° C. Interval sampling was conducted to determine OD600 and enzymatic activity.

The enzymatic activity was characterized by employing a 200 μL reaction system with 0.3% (w/v) sodium alginate as substrate to react for a period of 20 min, inactivating by boiling for 2 min and then determining the content of reducing sugar in the product by the DNS method.

Figure 4A:
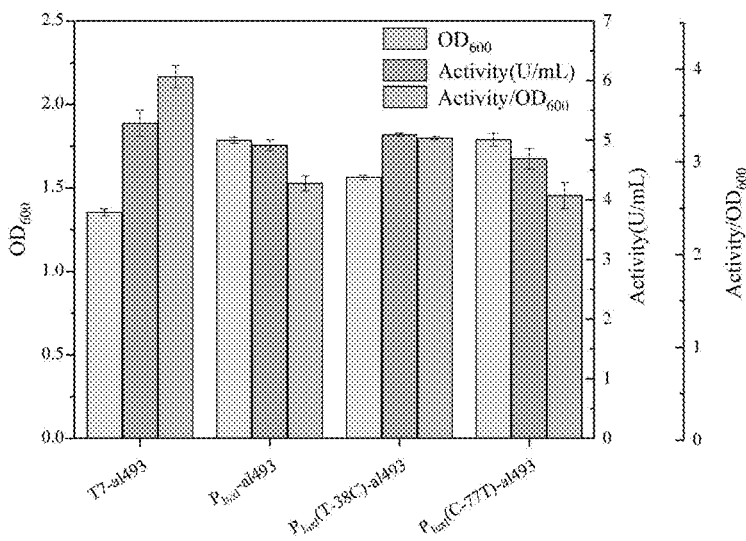
FIG. 4A-B are schematic diagrams showing the results of the expression of alginate lyase and esterase regulated by an auto-induction dynamic regulatory system and a modified system thereof, wherein, FIG. 4A, alginate lyaseAL493.

The results were shown in FIG. 4A and Table 2. The experimental results showed that: the enzymatic activity of $P_{J23100}$-luxIR-$P_{luxI}$(T-38C)-al493 strain and the enzymatic activity per cell density were relatively high, where the enzymatic activity was 5.090 U/mL, which was 96.37% that of the control group, and the enzymatic activity per cell density was 3.240 U/mL, which was 83.06% that of the control group.

TABLE 2

Result summary of regulation on the expression of alginate
lyase and esterase by an auto-induction dynamic regulatory
system and a modified system thereof

| Strains | Highest enzymatic activity (U/mL) | Enzymatic activity/OD600 | OD600 |
|---|---|---|---|
| T7-al493 | 5.282 | 3.901 | 1.354 |
| $P_{J23100}$-luxIR-$P_{luxI}$-al493 | 4.914 | 2.752 | 1.786 |
| $P_{J23100}$-luxIR-$P_{luxI}$(T-38C)-al493 | 5.090 | 3.240 | 1.563 |
| $P_{J23100}$-luxIR-$P_{luxI}$(C-77T)-al493 | 4.689 | 2.622 | 1.789 |
| T7-est7 | 3.284 | 2.443 | 1.341 |
| $P_{J23100}$-luxIR-$P_{luxI}$-est7 | 1.380 | 0.757 | 1.824 |
| $P_{J23100}$-luxIR-$P_{luxI}$(T-38C)-est7 | 1.497 | 1.079 | 1.387 |
| $P_{J23100}$-luxIR-$P_{luxI}$(C-77T)-est7 | 3.499 | 2.454 | 1.427 |

Embodiment 5 Application of $P_{luxI}$ Mutants in the Expression of Esterase Est7

The quorum sensing system with three promoters $P_{luxI}$, $P_{luxI}$(T-38C) and $P_{luxI}$(C-77T) was applied in the expression of esterase Est7 (whose nucleotide sequence was set forth in SEQ ID NO 13, and whose amino acid sequence was set forth in SEQ ID NO 18), so as to construct strains $P_{J23100}$-luxIR-$P_{luxI}$-est7 (the complete sequence of the constructed related gene was set forth in SEQ ID NO 20), $P_{J23100}$-luxIR-$P_{luxI}$(T-38C)-est7 and $P_{J23100}$-luxIR-$P_{luxI}$(C-77T)-est7, while using the fermentation culture results of T7-est7 as control. The strains regulated by the quorum sensing system were cultured at 20° C., while the strains regulated by T7 promoter needed to be firstly cultured at 37° C. to an OD600 of 0.6 and induced by adding IPTG with a final concentration of 0.5‰, and then the culture temperature was changed to 20° C. Interval sampling was conducted to determine OD600 and enzymatic activity.

The reaction substrate for esterase Est7 was a mixed solution of 20 mM p-nitrophenol laurate (pNPL) dissolved in isopropanol and DMSO (3:1). During the reaction, 460 μL of 100 mM Tris-HCl at pH 7.5 was firstly added as the buffer of the reaction, mixed with 20 μL of crude enzyme fluid and then incubated at 37° C. for 5 min. Then, 20 μL of reaction substrate was added to react in a water bath at 37° C. for 5 min. Finally, 500 μL of 1% SDS was added to terminate the reaction, and absorbance was determined at a wavelength of 405 nm.

Figure 4B:
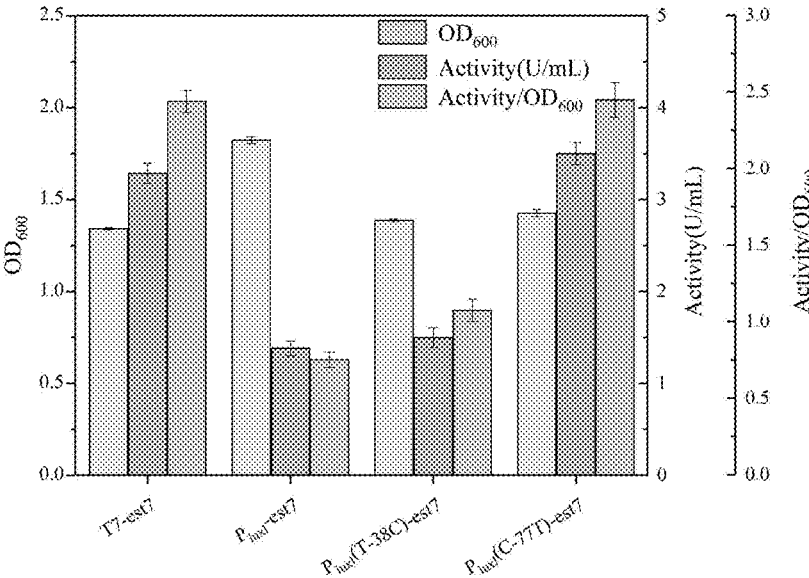

The results were shown in FIG. 4B and Table 2. The experimental results showed that: the enzymatic activity of $P_{J23100}$-luxIR-$P_{luxI}$(C-77T)-est7 and the enzymatic activity per cell density were relatively high, where the highest value of enzymatic activity was 3.499 U/mL, which was 106.55% that of the control group, and the enzymatic activity per cell density was 2.454 U/mL.

Embodiment 6 High-Density Fermentation of Alginate Lyase AL493

High-density fermentation was conducted in a 5 L fermenter, while controlling pH at 7.0 and the stirring speed at 300 rpm. The initial medium for fermentation culture was LB medium (10 g/L of peptone, 5 g/L of yeast powder, and 10 g/L of sodium chloride) and 10 g/L of glucose. Glucose dry powder was supplemented every 12 h to a final concentration of 10 g/L. $P_{J23100}$-luxIR-$P_{luxI}$(T-38C)-al493 strains were cultured at 20° C., while T7-al493 strains needed to be firstly cultured at 37° C. to an OD600 of 0.6 and induced by adding IPTG with a final concentration of 0.5‰, and then the culture temperature was changed to 20° C. Interval sampling was conducted every 12 h to determine OD600 and enzymatic activity.

Figure 5A:
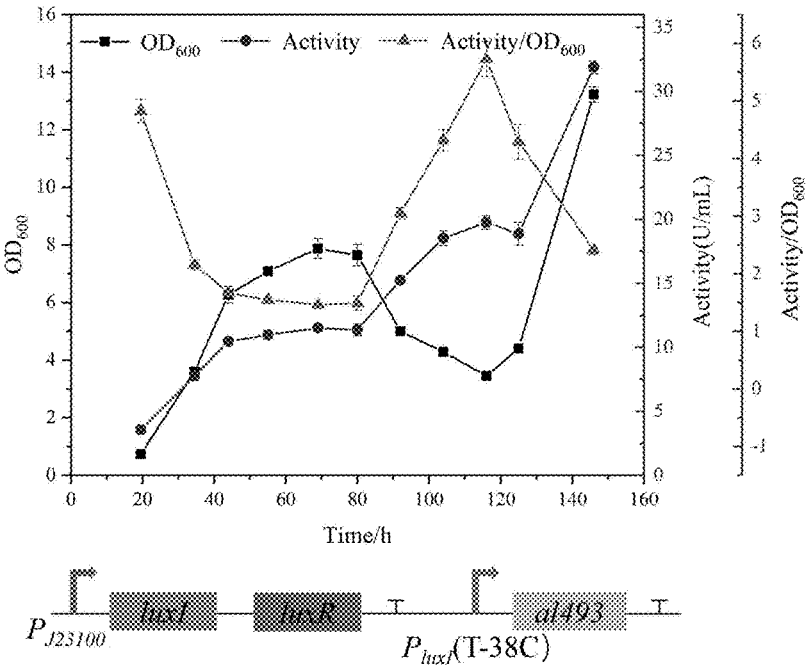
FIG. 5A-B are schematic diagrams showing the results of high-density fermentation of alginate lyase, wherein, FIG. 5A, $P_{luxI}$-luxIR-$P_{luxI}$(T-38C)-al493.
Figure 5B:
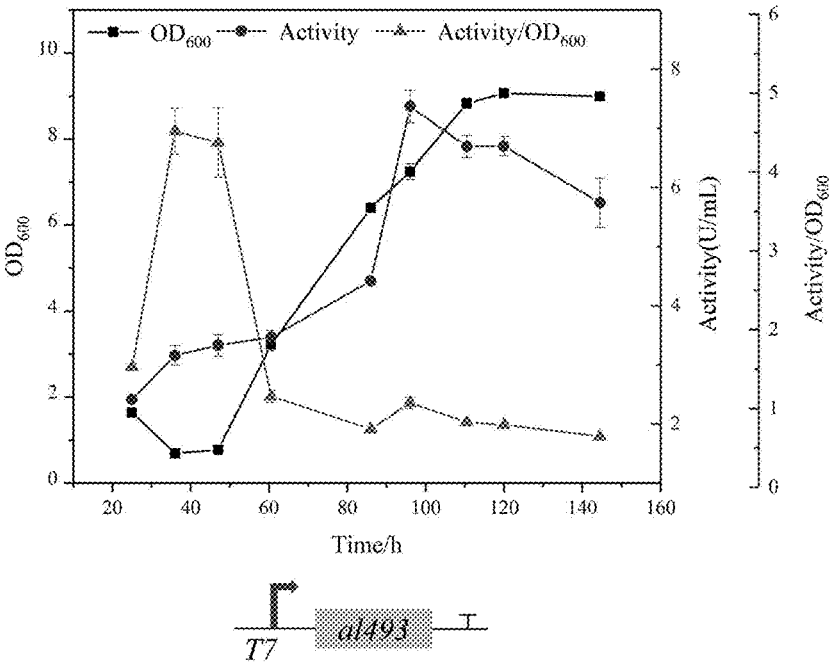

The results were shown in FIGS. 5A-B and Table 3. The experimental results showed that: $P_{J23100}$-luxIR-$P_{luxI}$(T-38C)-al493 strains could grow to higher bacterial density, which was 1.46 times that of the control group. At the same time, the highest enzymatic activity of $P_{J23100}$-luxIR-$P_{luxI}$ (T-38C)-al493 was 31.878 U/mL, which was 4.33 times that of the control group.

TABLE 3

Summary of high-density fermentation results of alginate lyase

| Strains | Highest OD$_{600}$ | Highest enzymatic activity (U/mL) |
|---|---|---|
| T7-al493 | 9.067 | 7.367 |
| $P_{J23100}$-luxIR-$P_{luxI}$(T-38C)-al493 | 13.227 | 31.878 |

The above embodiments are provided to those skilled in the art to completely disclose and describe how to implement and use the claimed embodiments, rather than limiting the scope disclosed herein. Modifications apparent to those skilled in the art shall be covered within the scope of the attached claims.

What is claimed is:

1. An auto-induction regulatory system based on quorum sensing, wherein: the system comprises luxI, luxR and egfp, a promoter for controlling the expression of luxI and luxR, and a promoter for controlling the expression of egfp, wherein, the promoter for controlling the expression of luxI and luxR is $P_{luxI}$, $P_{BB}$ Or $P_{J23100}$; and the promoter for controlling the expression of egfp is $P_{luxI}$(C-77T), where the nucleotide sequence of said $P_{luxI}$(C-77T) is as set forth in SEQ ID NO: 5.

2. The auto-induction regulatory system based on quorum sensing according to claim 1, wherein:

the nucleotide sequence of said $P_{luxI}$ is as set forth in SEQ ID NO: 1;

the nucleotide sequence of said $P_{BB}$ is as set forth in SEQ ID NO: 2;

the nucleotide sequence of said $P_{J23100}$ is as set forth in SEQ ID NO: 3;

and the nucleotide sequences of said luxI, luxR and egfp are as set forth in SEQ ID NO: 9, SEQ ID NO: 10, and SEQ ID NO: 11.

3. An engineered bacterium containing the auto-induction regulatory system based on quorum sensing according to claim 1.

4. A recombinant expression vector, whose structure is $P_{luxI}$-luxI-luxR-$P_{luxI}$(C-77T)-est7, wherein, the nucleotide sequence of said $P_{luxI}$ is as set forth in SEQ ID NO: 1;

the nucleotide sequence of said $P_{luxI}$(C-77T) is as set forth in SEQ ID NO: 5;

the nucleotide sequence of said luxI is as set forth in SEQ ID NO: 9, and the nucleotide sequence of said luxR is as set forth in SEQ ID NO: 10;

and the nucleotide sequence of said est7 is as set forth in SEQ ID NO: 13.

5. A recombinant engineered bacterium comprising the recombinant expression vector according to claim 4 in its genome.

\* \* \* \* \*